United States Patent
Komori

(10) Patent No.: US 12,136,216 B2
(45) Date of Patent: Nov. 5, 2024

(54) IMAGE PROCESSING DEVICE AND IMAGE PROCESSING PROGRAM

(71) Applicant: FUJIFILM CORPORATION, Tokyo (JP)

(72) Inventor: Yuichi Komori, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 431 days.

(21) Appl. No.: 17/488,333

(22) Filed: Sep. 29, 2021

(65) Prior Publication Data

US 2022/0101529 A1 Mar. 31, 2022

(30) Foreign Application Priority Data

Sep. 30, 2020 (JP) .................................. 2020-166471

(51) Int. Cl.
*G06T 7/00* (2017.01)
*A61B 5/00* (2006.01)
(Continued)

(52) U.S. Cl.
CPC ............ *G06T 7/0014* (2013.01); *A61B 5/708* (2013.01); *A61B 6/0414* (2013.01); *A61B 6/502* (2013.01);
(Continued)

(58) Field of Classification Search
CPC ......... G06T 7/0014; G06T 2207/30068; A61B 5/708; A61B 6/0414; A61B 6/502;
(Continued)

(56) References Cited

U.S. PATENT DOCUMENTS

2017/0172531 A1* 6/2017 Sugiyama ............ A61B 6/0414

FOREIGN PATENT DOCUMENTS

| JP | 2007-236805 A | 9/2007 |
| JP | 2008-086389 A | 4/2008 |

(Continued)

OTHER PUBLICATIONS

English language translation of the following: Office action dated Apr. 25, 2023 from the JPO in a Japanese patent application No. 2020-166471 corresponding to the instant patent application. This office action translation is submitted now in order to supplement the understanding of the cited references which are being disclosed in the instant Information Disclosure Statement.

*Primary Examiner* — Zhitong Chen
(74) *Attorney, Agent, or Firm* — SOLARIS Intellectual Property Group, PLLC

(57) ABSTRACT

An image processing device including: at least one processor, wherein the processor is configured to select an image used to guide positioning of a breast to be imaged by a mammography apparatus, which irradiates the breast compressed by a compression member with radiation to capture a radiographic image, from a plurality of images of the breast on the basis of imaging information related to a capture of the plurality of images, generate a projection image for guiding the positioning of the breast to be imaged from the selected image, and control the mammography apparatus such that an image projection unit projects the generated projection image for guidance.

12 Claims, 9 Drawing Sheets

(51) Int. Cl.
*A61B 6/00* (2006.01)
*A61B 6/04* (2006.01)
*A61B 6/50* (2024.01)
*G06V 10/40* (2022.01)

(52) U.S. Cl.
CPC ................ *A61B 6/54* (2013.01); *G06V 10/40* (2022.01); *G06T 2207/30068* (2013.01)

(58) Field of Classification Search
CPC ........... A61B 6/54; A61B 6/0492; A61B 6/46; G06V 10/40; G06V 2201/03
See application file for complete search history.

(56) References Cited

FOREIGN PATENT DOCUMENTS

| | | | |
|---|---|---|---|
| JP | 2009-291336 A | 12/2009 | |
| JP | 4833785 B2 * | 12/2011 | ............. A61B 5/103 |
| JP | 2017-113540 A | 6/2017 | |

* cited by examiner

FIG. 6

```
PRIORITY SETTING PROCESS
        START
           │
           ▼
┌──────────────────────────┐
│ DISPLAY PRIORITY SETTING │─── S10
│       INFORMATION        │
└──────────────────────────┘
           │
           ▼
┌──────────────────────────┐
│ RECEIVE SETTING OF PRIORITY │─── S12
└──────────────────────────┘
           │
           ▼
┌──────────────────────────┐
│ STORE PRIORITY INFORMATION │─── S14
└──────────────────────────┘
           │
           ▼
          END
```

FIG. 7

| SELECTION CRITERIA | PRIORITY |
|---|---|
| IMAGE OF OPPOSITE BREAST CAPTURED MOST RECENTLY (WITHIN 1 HOUR) | 1 |
| BREAST ON SAME SIDE | 2 |
| ORDER OF SCORE | 4 |
| CC OR MLC IS MATCHED | 3 |
| TYPE OF COMPRESSION PLATE IS MATCHED | - |
| IMAGE CAPTURED MOST RECENTLY | 5 |

IMAGE PROCESSING DEVICE AND IMAGE PROCESSING PROGRAM

CROSS-REFERENCE TO RELATED APPLICATION

The present application claims priority under 35 U.S.C. § 119 to Japanese Patent Application No. 2020-166471 filed on Sep. 30, 2020. The above application is hereby expressly incorporated by reference, in its entirety, into the present application.

BACKGROUND

Technical Field

The present disclosure relates to an image processing device and a non-transitory computer-readable storage medium storing an image processing program.

Description of the Related Art

A mammography apparatus is known which irradiates a breast compressed by a compression member with radiation to capture a radiographic image. In a case in which imaging is performed, for example, information for guiding the positioning of the breast may be displayed. For example, JP2008-086389A discloses a technique which generates an image indicating a skin line of a breast from a radiographic image captured in the past, displays the generated image indicating the skin line on an LCD, and displays a projection image on a projection surface of a compression member.

In a case in which there are a plurality of radiographic images captured in the past, it may be difficult to appropriately select a radiographic image used to generate a projection image for guidance to be projected in the current imaging of the breast from the plurality of radiographic images. In a case in which an appropriate radiographic image is not selected, the breast is not positioned in an appropriate state even though the breast is positioned with reference to the generated projection image.

The present disclosure has been made in view of the above-mentioned problems, and an object of the present disclosure is to provide an image processing device and a non-transitory computer-readable storage medium storing an image processing program that can project a projection image for guidance generated by an appropriate radiographic image selected from a plurality of radiographic images captured in the past in the current imaging.

SUMMARY

In order to achieve the above object, according to a first aspect of the present disclosure, there is provided an image processing device comprising at least one processor. The processor is configured to select an image used to guide positioning of a breast to be imaged by a mammography apparatus, which irradiates the breast compressed by a compression member with radiation to capture a radiographic image, from a plurality of images of the breast on the basis of imaging information related to a capture of the plurality of images, generate a projection image for guiding the positioning of the breast to be imaged from the selected image, and control the mammography apparatus such that an image projection unit projects the generated projection image for guidance.

According to a second aspect of the present disclosure, in the image processing device according to the first aspect, the imaging information may include information indicating a subject with the breast to be imaged, and the processor may select an image of the breast of the same subject as the subject with the breast to be imaged from the plurality of images.

According to a third aspect of the present disclosure, in the image processing device according to the first aspect, the imaging information may include information indicating an imaging date and time, and the processor may select an image with a latest imaging date and time from the plurality of images.

According to a fourth aspect of the present disclosure, in the image processing device according to the third aspect, the imaging information may further include information indicating whether the breast to be imaged is a left breast or a right breast of the subject. In a case in which left and right sides of the breast of the selected image and the breast to be imaged are opposite to each other, the processor may generate the projection image for guidance in which the left and right sides of the selected image are reversed.

According to a fifth aspect of the present disclosure, in the image processing device according to the first aspect, the imaging information may include information indicating whether or not each of left and right breasts of the subject is imaged by a series of imaging operations of the mammography apparatus. In a case in which the series of imaging operations is performed and the plurality of images include a radiographic image captured first by the series of imaging operations, the processor may select the radiographic image captured first and reverse left and right sides of the selected image to generate the projection image for guidance.

According to a sixth aspect of the present disclosure, in the image processing device according to the fourth aspect, after reversing the left and right sides of the selected image, the processor may extract a feature image indicating a shape feature of the breast from the reversed image to obtain the projection image for guidance.

According to a seventh aspect of the present disclosure, in the image processing device according to the fourth aspect, the processor may extract a feature image indicating a shape feature of the breast from the selected image and reverse the extracted feature image to generate the projection image for guidance.

According to an eighth aspect of the present disclosure, in the image processing device according to the first aspect, the processor may select an image having the same imaging information as that in imaging to be performed from the plurality of images.

According to a ninth aspect of the present disclosure, in the image processing device according to the first aspect, the processor may score each of the plurality of images on the basis of the imaging information and select an image with a highest score from the plurality of images.

According to a tenth aspect of the present disclosure, in the image processing device according to the first aspect, the processor may receive a setting of a priority of a selection criterion of selecting the image used for guidance on the basis of the imaging information and select the image used for guidance which satisfies the selection criterion from the plurality of images on the basis of the priority.

According to an eleventh aspect of the present disclosure, in the image processing device according to the first aspect, the imaging information may be information indicating at least one of an imaging date and time, a subject corresponding to the breast, a compression pressure applied to the breast, whether the breast is a left breast or a right breast, or an imaging direction.

According to a twelfth aspect of the present disclosure, in the image processing device according to the first aspect, the projection image for guidance may be an image for guiding at least one of a shape of the breast in the compressed state or a position of the breast in the compressed state.

Further, in order to achieve the above object, according to a thirteenth aspect of the present disclosure, there is provided a non-transitory computer-readable storage medium storing an image processing program that causes a computer to perform a process comprising: selecting an image used to guide positioning of a breast to be imaged by a mammography apparatus, which irradiates the breast compressed by a compression member with radiation to capture a radiographic image, from a plurality of images of the breast on the basis of imaging information related to a capture of the plurality of images; generating a projection image for guiding the positioning of the breast to be imaged from the selected image; and controlling the mammography apparatus such that an image projection unit projects the generated projection image for guidance.

According to the present disclosure, it is possible to project a projection image for guidance generated by an appropriate radiographic image selected from a plurality of radiographic images captured in the past in the current imaging.

BRIEF DESCRIPTION OF THE DRAWINGS

Exemplary embodiments according to the technique of the present disclosure will be described in detail based on the following figures, wherein:

FIG. 6 is a flowchart illustrating an example of the flow of a priority setting process.

FIG. 7 is a diagram illustrating an example of priority setting information displayed on a display unit.

DETAILED DESCRIPTION

Hereinafter, embodiments of the present disclosure will be described in detail with reference to the drawings. In addition, each of the embodiments does not limit the present disclosure.

First Embodiment

Figure 1:
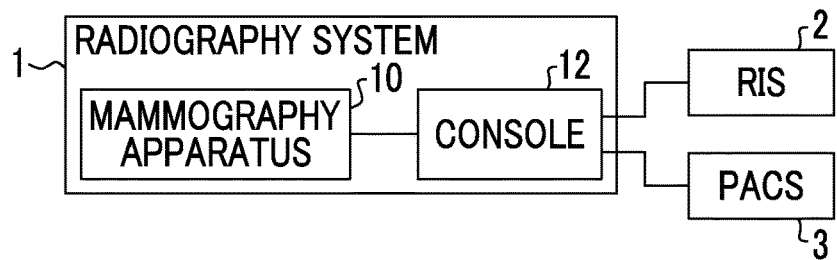
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The console 12 according to this embodiment is an example of an image processing device according to the present disclosure.

Figure 2A:
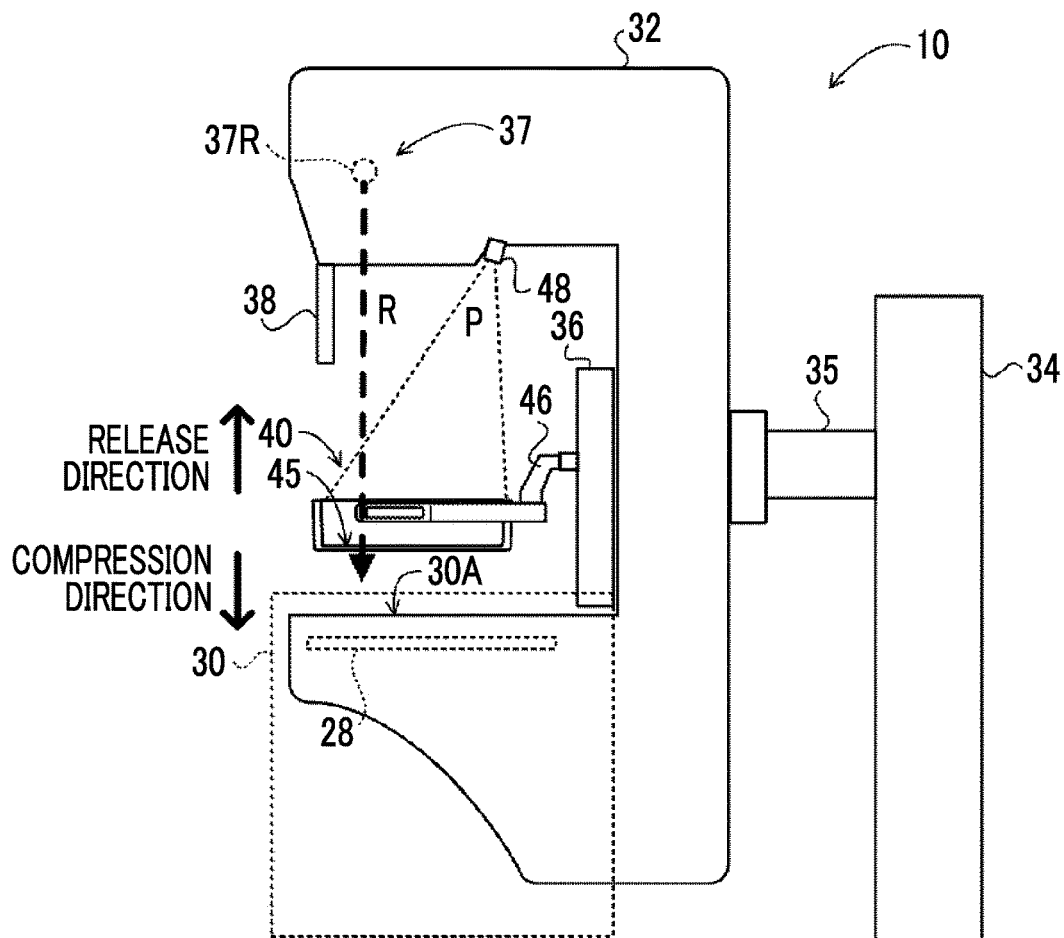
FIG. 2A is a side view illustrating an example of the outward appearance of a mammography apparatus according to the embodiment.
Figure 3:
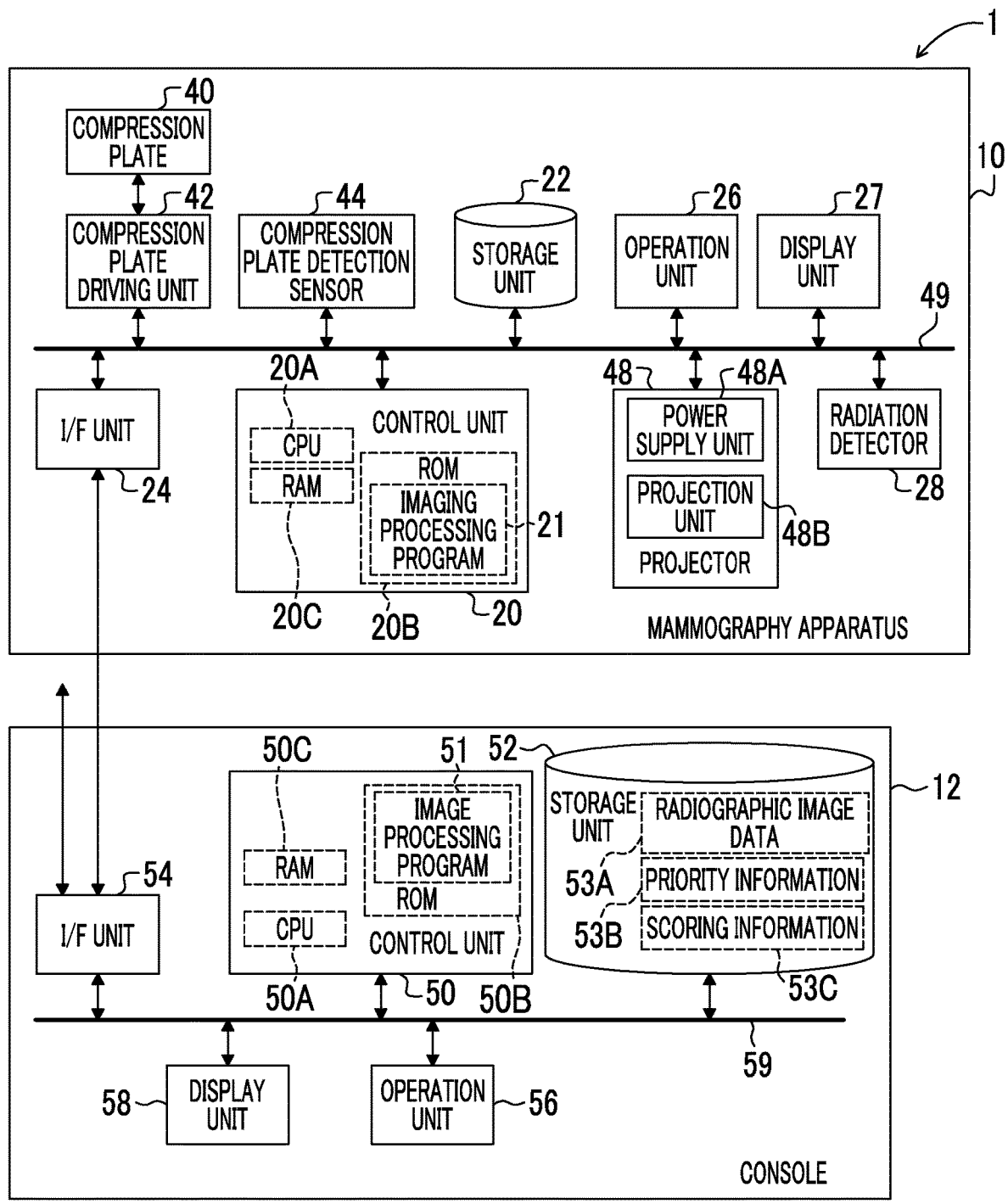
FIG. 3 is a block diagram illustrating an example of the configuration of the mammography apparatus and a console according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 3 is a functional block diagram illustrating an example of the configuration of the mammography apparatus 10 and the console 12 according to this embodiment.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting on, for example, a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. The face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in the up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 37R in a case in which the radiation R is emitted from the radiation source 37R to the imaging table 30 in the capture of a radiographic image is referred to as an "imaging position".

In a case in which the CC imaging is performed, the imaging surface 30A is adjusted to a state in which the imaging surface 30A faces the upper side of the mammography apparatus 10 (the head of the subject). Further, in this case, the position of the radiation source 37R is adjusted to the imaging position that faces the imaging surface 30A of the imaging table 30. Therefore, the radiation R is emitted from the radiation source 37R to the breast in a direction from the head to the foot of the subject, and the CC imaging is performed.

In contrast, in a case in which the MLO imaging is performed, the position of the imaging table 30 is adjusted to a state in which the imaging surface 30A is rotated up to a predetermined angle in a range of, for example, 45 degrees or more and less than 90 degrees with respect to the case in which the CC imaging is performed. Specifically, in a case in which an image of the left breast is captured, the imaging surface 30A is inclined to the right. In a case in which an image of the right breast is captured, the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 3) that moves a compression plate 40 compressing the breast in the up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit to compress the breast of the subject between the compression plate 40 and the imaging table 30. The reason why the breast is compressed by the compression plate 40 is, for example, to expand the overlap of the mammary gland tissues to make it easy to determine whether the mammary gland tissue is a benign lesion or a malignant lesion, to suppress the blurring of a radiographic image to make it easy to see a mammary gland structure or the like, to fix the breast to suppress the body movement of the subject, and to decrease the thickness of the breast to reduce the radiation exposure of the breast. As illustrated in FIG. 2A, for the movement direction of the compression plate 40, the direction in which the breast is compressed, that is, the direction in which the compression plate 40 becomes closer to the imaging surface 30A is referred to as a "compression direction", and the direction in which the compression of the breast is released, that is, the direction in which the compression plate 40 becomes closer to the radiation emitting unit 37 is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression plate detection sensor (see a compression plate detection sensor 44 in FIG. 3). The compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2B:
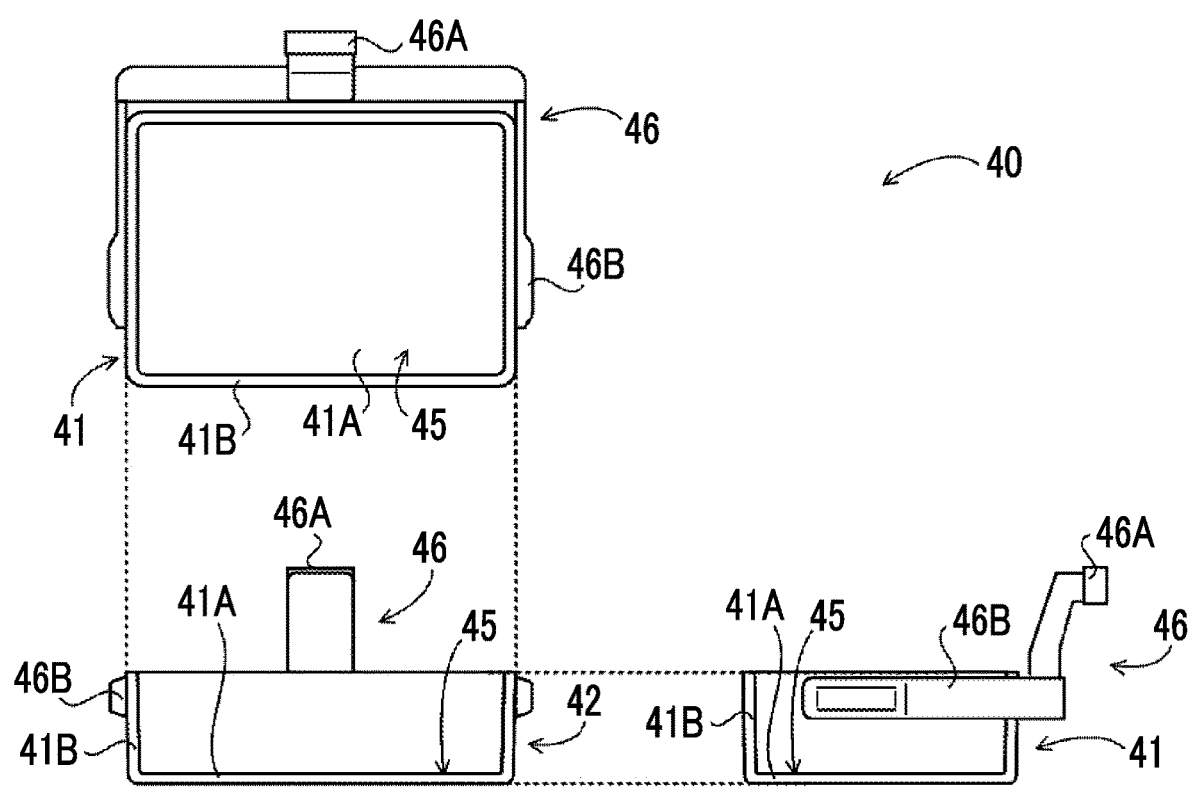
FIG. 2B is a three-view diagram illustrating an example of a compression plate according to the embodiment.

As a specific example, the compression plate 40 that can be attached to the mammography apparatus 10 according to this embodiment will be described with reference to FIG. 2B. FIG. 2B is a three-view diagram illustrating an example of the compression plate 40 according to this embodiment. The three-view diagram illustrated in FIG. 2B includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2B, the compression plate 40 according to this embodiment includes a compression portion 41 and the support portion 46.

The compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height. The compression portion 41 has a projection surface 45 onto which a projection image P for guidance is projected by a projector 48 which will be described below. For example, in this embodiment, a surface (upper surface) of the bottom portion 41A of the compression portion 41 which faces the radiation emitting unit 37 is the projection surface 45. In addition, for example, the position of the projection surface 45 of the compression plate 40 is not limited to this aspect. For example, the projection surface 45 may be a surface of the bottom portion 41A of the compression portion 41 which comes into contact with the breast or a surface of the wall portion 41B.

It is preferable that the compression plate 40 is optically transparent in order to check positioning or a compressed state. In addition, the compression plate 40 is made of a material having high transmittance for the radiation R. Further, in a case in which light is incident on the projection surface 45, most of the light (for example, 90%) is transmitted and a portion (for example, 10%) of the light is specularly reflected from the surface of an object such that an incident angle and a reflection angle are equal to each other, in order to display an image corresponding to the projection image P for guidance projected from the projector 48. For example, a surface of the bottom portion 41A of the compression plate 40 which faces the radiation source 37R may be roughened to form the projection surface 45. In addition, for example, a specular reflection sheet may be attached to the surface of the compression plate 40 to form the projection surface 45. Further, in a case in which the projection surface 45 is a smooth surface such as a case in which a specular reflection sheet is attached, a surface of the compression plate 40 that comes into contact with the subject, such as the breast, may be the projection surface 45.

On the other hand, the support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

Further, the projector 48 that projects the projection image P for guidance onto the projection surface 45 of the compression plate 40 is provided at a position of the arm portion 32 which is away from the subject below the radiation emitting unit 37. The projector 48 according to this embodiment is an example of an image projection unit according to the present disclosure. Known projectors, such as a liquid crystal projector, a Digital Light Processing (DLP) (registered trademark) projector, and a laser projector, can be used as the projector 48. As illustrated in FIG. 3, the projector 48 according to this embodiment includes a power supply unit 48A and a projection unit 48B. In the projector 48, the turn-on and turn-off of the power supply unit 48A are controlled in response to an instruction from a control unit 20 which will be described below. Further, the projection image P for guidance is projected from the projection unit 48B onto the projection surface 45 of the compression plate 40 in response to an instruction from the control unit 20.

Furthermore, the control unit 20, a storage unit 22, an interface (I/F) unit 24, an operation unit 26, and a display unit 27 illustrated in FIG. 3 are provided in the imaging table 30 of the mammography apparatus 10 according to this embodiment. The control unit 20, the storage unit 22, the I/F unit 24, the operation unit 26, the display unit 27, the radiation detector 28, the compression plate driving unit 42, the compression plate detection sensor 44, and the projector 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including an image processing program 51 (which will be described below) executed by the CPU 50A are stored in the ROM 50B in advance. The RAM 50C temporarily stores various kinds of data. The CPU 50A according to this embodiment is an example of a processor according to the present disclosure. The image processing program 51 according to this embodiment includes an image processing program for performing image processing, a priority setting processing program for performing a priority setting process, and a scoring processing program for performing a scoring process, which will be described in detail below. The image processing program 51 according to this embodiment is an example of an image processing program according to the present disclosure.

The storage unit 52 stores radiographic image data 53A of the radiographic image captured by the mammography apparatus 10, priority information 53B which will be described in detail below, scoring information 53C which will be described in detail below, and various other kinds of information. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 performs the communication of various kinds of information among the mammography apparatus 10, the RIS 2, and a picture archiving and communication system (PACS) 3 using wireless communication or wired communication. In the radiography system 1 according to this embodiment, the image data of the radiographic image captured by the mammography apparatus 10 is received from the mammography apparatus 10 through the I/F unit 54 by wireless communication or wired communication and is stored as the radiographic image data 53A in the storage unit 52. Then, the image data is transmitted to the PACS 3 through the I/F unit 54 by wireless communication and is then accumulated in the PACS 3.

Figure 4:
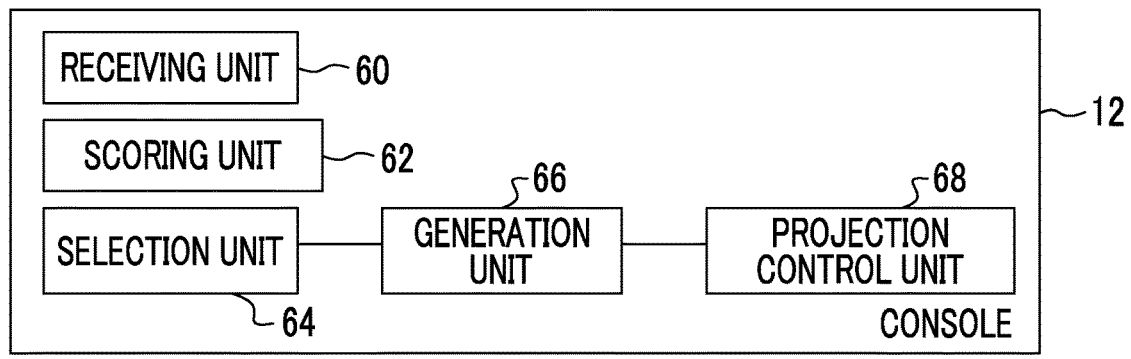
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a receiving unit 60, a scoring unit 62, a selection unit 64, a generation unit 66, and a projection control unit 68. For example, in the console 12 according to this embodiment, the CPU 50A of the control unit 50 executes the image processing program included in the image processing program 51 stored in the ROM 50B to function as the selection unit 64, the generation unit 66, and the projection control unit 68.

The selection unit 64 has a function of selecting a radiographic image used to guide the positioning of the breast to be imaged from a plurality of radiographic images of the breast on the basis of imaging information related to the capture of each of the plurality of radiographic images. In a case in which imaging is performed by the mammography apparatus 10 as described above, the user positions the breast of the subject on the imaging surface 30A of the imaging table 30, and the breast is compressed by the compression plate 40. It is desirable to position the breast in an appropriate state. Specifically, it is desirable that the shape and position of the breast compressed by the compression plate 40 are appropriate. For example, in a case in which radiographic images are interpreted, the interpretation may be performed while comparing the radiographic image of the breast of the subject captured in the past with the radiographic image of the breast of the subject captured this time. In a case in which the positioning state of the breast is the same in the radiographic image captured in the past and the radiographic image captured this time, it is easy to compare the two radiographic images.

Therefore, in this embodiment, the projector 48 projects the projection image P for guiding positioning. For example, in this embodiment, a projection image P for guiding at least one of the shape or position of the breast in the compressed state is applied as the projection image P for guiding positioning. Specifically, the projector 48 projects a projection image P indicating the skin line of the breast in the compressed state as the projection image P for guiding positioning onto the projection surface 45 of the compression plate 40. The user positions the breast with reference to the skin line of the breast displayed on the projection surface 45 of the compression plate 40 and compresses the breast with the compression plate 40. In addition, the projection image P for guidance according to this embodiment is an example of a projection image for guidance according to the present disclosure.

In this embodiment, the projection image P for guidance to be projected in the current imaging is generated from the radiographic image of the breast captured in the past. The selection unit 64 has a function of selecting a radiographic image suitable to generate the projection image P for guiding positioning in the current imaging on the basis of the imaging information in a case in which the breast was imaged in the past. Specifically, the selection unit 64 selects a radiographic image satisfying selection criteria from a plurality of radiographic images captured in the past on the basis of the priority information 53B stored in the storage unit 52.

The radiographic image selected by the selection unit 64 is output to the generation unit 66. In addition, examples of the imaging information include information related to an imaging date and time, information indicating the subject pertaining to the breast, information indicating the compression pressure of the compression plate 40 against the breast, information indicating which of the left and right breasts is the object to be imaged, and information indicating an imaging direction such as CC imaging, MLO imaging, or the angle of the arm portion 32. However, the present disclosure is not limited thereto.

The generation unit 66 has a function of generating the projection image P for guiding the positioning of the breast to be imaged this time from the radiographic image selected by the selection unit 64. For example, the generation unit 66 according to this embodiment generates a projection image indicating the skin line of the breast from the radiographic image as the projection image P for guiding positioning as described above. The projection image P for guidance generated by the generation unit 66 is output to the projection control unit 68. A method for generating the projection image P for guidance in the generation unit 66 is not limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line. In addition, for example, JP2010-051456A discloses a method which divides a radiographic image of the breast into a breast region and a blank region on the basis of the density of each pixel of the radiographic image and connects the pixels which are the boundary points between the breast region and the blank region to generate a skin line.

In a case in which the selected radiographic image is larger than the projection surface 45, the generation unit 66 may generate the projection image P for guidance indicating the skin line based on the shape of the breast indicated by a partial region of the radiographic image which corresponds to the size of the projection surface 45. In other words, the generation unit 66 may cut a partial region corresponding to the size of the projection surface 45 in the selected radiographic image and generate the projection image P for guidance indicating the skin line on the basis of the cut image. In addition, in many cases, the mammography apparatus 10 captures an image including the chest wall side. Therefore, the region to be cut is preferably a partial region on the chest wall side. Further, it is preferable that the region to be cut is a partial region including the center of the shape of the breast included in the radiographic image in the left-right direction.

Furthermore, in a case in which the selected radiographic image is smaller than the projection surface 45, the generation unit 66 may generate the projection image P for guidance which indicates a skin line and in which the shape of the breast outside the radiographic image has been complemented on the basis of the shape of the breast indicated by the radiographic image. A known image complementing method can be applied as the complementing method. For example, the generation unit 66 may complement an extension line on the basis of the curvature of the skin line of a portion generated on the basis of the selected radiographic image. Further, for example, the generation unit 66 may complement a tangent line to the skin line of the portion generated on the basis of the radiographic image as the extension line.

Furthermore, in a case in which the size of the selected radiographic image and the size of the projection surface 45 are not matched with each other, the generation unit 66 may generate the projection image P for guidance which indicates the skin line based on the shape of the breast indicated by an image obtained by enlarging or reducing the selected radiographic image according to the size of the projection surface 45. For example, an enlargement and reduction ratio may be predetermined for each combination of the size of the radiographic image and the size of the projection surface 45.

Moreover, the generation unit 66 may extract a skin line image indicating the skin line from the radiographic image, use the extracted skin line image as the projection image P for guidance, and generate the projection image P for guidance from the extracted skin line image. The skin line according to this embodiment is an example of a shape feature of the breast according to the present disclosure, and the skin line image is an example of a feature image according to the present disclosure.

For an example of a method for generating the projection image P for guidance in the generation unit 66, a case in which, in the current imaging of the left breast, the projection image P for guidance is generated from the radiographic image of the right breast of the subject captured most recently will be described as an example.

Figure 5A:
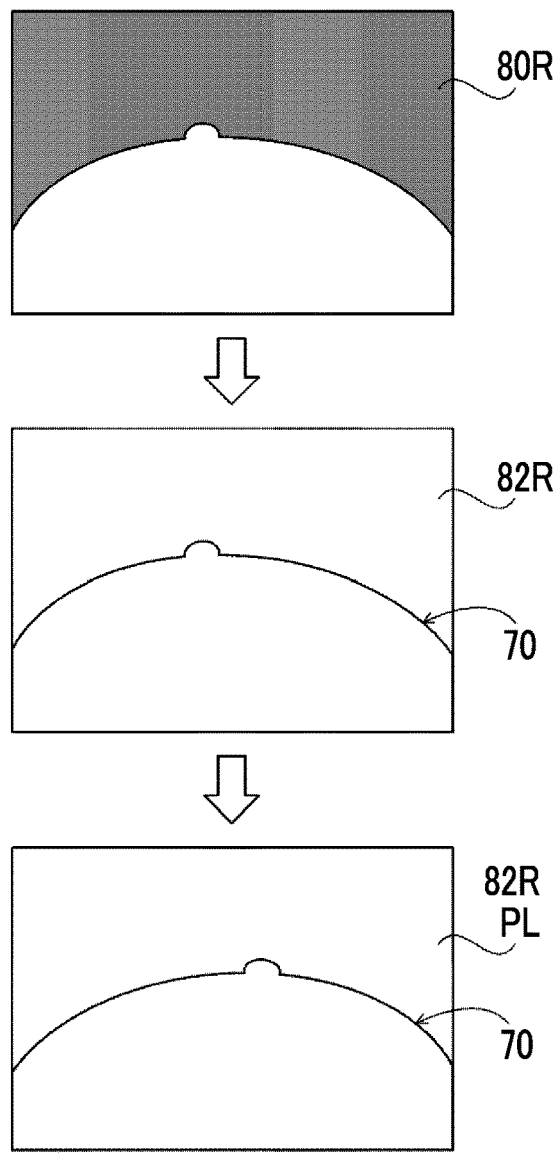
FIG. 5A is a diagram illustrating an example of a first generation method for generating a projection image for guiding a left breast from a radiographic image of a right breast.

In this case, the selection unit 64 selects the radiographic image of the right breast of the subject captured most recently. FIG. 5A illustrates an example of a first generation method for generating the projection image P for guiding the left breast from the radiographic image of the right breast. The generation unit 66 generates a skin line image 82R indicating a skin line 70 as the shape feature of the breast from a radiographic image 80R of the right breast. Then, the generation unit 66 generates an image obtained by reversing the generated skin line image 82R in a left-right direction as the projection image PL for guidance in the imaging of the left breast.

Figure 5B:
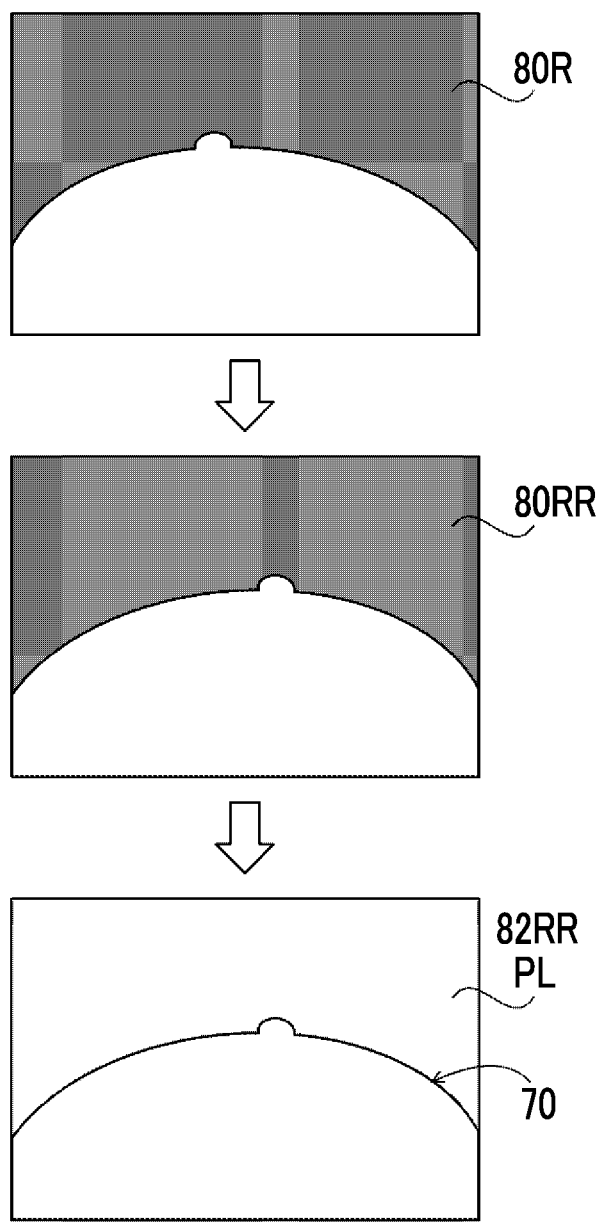
FIG. 5B is a diagram illustrating an example of a second generation method for generating a projection image for guiding the left breast from the radiographic image of the right breast.

In addition, FIG. 5B illustrates an example of a second generation method for generating the projection image P for guiding the left breast from the radiographic image of the right breast. First, the generation unit 66 reverses the left and right sides of the radiographic image 80R of the right breast and generates a skin line image 82RR indicating the skin line 70 as the shape feature of the breast from a radiographic image 80RR of the right breast reversed in the left-right direction. The generation unit 66 uses the generated skin line image 82RR as a projection image PL for guidance in the imaging of the left breast.

In accordance with the above, in either the first generation method described with reference to FIG. 5A or the second generation method described with reference to FIG. 5B, the generation unit 66 can generate the same projection image PL for guidance. In addition, which of the first generation method and the second generation method is applied is not particularly limited. For example, one of the two generation methods may be set in advance, or the generation methods may be switched by the user's request. Further, a method for reversing the left and right sides of the radiographic image or the skin line image is not particularly limited. For example, a method for reversing the left and right positions with respect to a pixel position may be applied.

The projection control unit 68 has a function of controlling the projector 48 of the mammography apparatus 10 such that the projection image P for guidance input from the generation unit 66 is projected. Specifically, projection image data indicating the projection image P for guidance input from the generation unit 66 is output to the mammography apparatus 10 through the I/F unit 54. In the mammography apparatus 10, in a case in which the projection image data is input, the control unit 20 performs control to direct the projection unit 48B of the projector 48 to project the projection image P for guidance corresponding to the projection image data. A display image corresponding to the projection image P for guidance is displayed on the projection surface 45 of the compression plate 40 attached to the compression unit 36 of the mammography apparatus 10 by this control.

In addition, in the console 12 according to this embodiment, the CPU 50A of the control unit 50 executes the priority setting processing program included in the image processing program 51 stored in the ROM 50B to function as the receiving unit 60.

The receiving unit 60 has a function of receiving the setting of the priority of the selection criteria for the selection unit 64 to select a radiographic image used to generate the projection image P for guidance from the radiographic images captured in the past on the basis of the imaging information. Information indicating the priority of the selection criteria received by the receiving unit 60 is stored as the priority information 53B in the storage unit 52.

Here, the operation of the console 12 related to the setting of the priority will be described. In the console 12 according to this embodiment, for example, the CPU 50A of the control unit 50 executes the priority setting processing program included in the image processing program 51 stored in the ROM 50B to perform the priority setting process whose example is illustrated in FIG. 6. FIG. 6 is a flowchart illustrating an example of the flow of the priority setting process performed in the console 12 according to this embodiment.

In Step S10 illustrated in FIG. 6, the receiving unit 60 directs the display unit 58 to display priority setting information for the user to set the priority. FIG. 7 illustrates an example of the priority setting information displayed on the display unit 58. As illustrated in FIG. 7, a list of a plurality of selection criteria as the priority setting information is displayed on the display unit 58. The user inputs the priority for each selection criterion using the operation unit 56 with reference to the plurality of selection criteria listed.

FIG. 7 illustrates an example of a state in which the user sets the priority of the selection criterion of selecting the image of the opposite breast captured most recently (within 1 hour) to first place, the priority of the selection criterion of selecting the image of the breast on the same side to second place, the priority of the selection criterion of selecting the image captured in the CC imaging or the MLO imaging that is the same as the current imaging to third place, the priority of the selection criterion of selecting the images in descending order of the score given by the scoring unit 62 to fourth place, and the priority of the selection criterion of selecting the radiographic image captured most recently to fifth place. Further, in the example illustrated in FIG. 7, the user does not set the ranking of the priority of the selection criterion of selecting the image captured in a state in which the breast is compressed by the same type of compression plate 40. In accordance with the above, the user may not set the priorities for all of the plurality of selection criteria displayed on the display unit 58 or may set the priorities only for the desired selection criteria.

In many cases, the left and right breasts of the same subject are symmetric with respect to the center line of the subject in the CC direction and are similar in size and shape. The selection criterion of selecting the image of the opposite breast captured most recently (within 1 hour) makes it possible to select a radiographic image indicating the appropriate shape of the breast corresponding to the current shape of the breast.

In many cases, one breast is bilaterally asymmetric in shape. Therefore, in some cases, the shape of the breast appearing in the radiographic image varies depending on the left and right breasts. Therefore, the selection criterion of selecting the image of the breast on the same side makes it possible to select a radiographic image indicating the appropriate shape of the breast corresponding to the left or right breast.

In addition, in some cases, the shape of the positioned breast is different between the CC imaging and the MLO imaging. For example, in some cases, the appearance of the chest wall is different between the CC imaging and the MLO imaging. Therefore, the selection criterion of selecting the image captured in the CC imaging or the MLO imaging that is the same as the current imaging makes it possible to select a radiographic image indicating the appropriate shape of the breast corresponding to the type of imaging.

Further, the selection criterion of selecting the image in descending order of the score given by the scoring unit 62 makes it possible to select a radiographic image determined to be appropriate from a plurality of viewpoints. Furthermore, it is possible to select an appropriate radiographic image corresponding to the user's preference depending on score setting.

In addition, according to the selection criterion of selecting the radiographic image captured most recently, for example, in a case in which a plurality of radiographic images of the breast of the subject on the same side or the left and right breasts of the subject are captured continuously, it is possible to select the radiographic image of the breast of the subject captured immediately before. It is possible to select the radiographic image of the breast closer to the current breast of the subject. Therefore, it is possible to select a radiographic image indicating the appropriate shape of the breast.

Then, in Step S12, the receiving unit 60 receives the setting of the priority for each selection criterion set by the user as described above. Then, in Step S14, the receiving unit 60 stores the setting of the priority for each selection criterion received in the Step S12 as the priority information 53B in the storage unit 52. In a case in which the process in Step S14 ends, the priority setting process illustrated in FIG. 6 ends.

In addition, the specific timing when the receiving unit 60 performs the priority setting process is not limited. For example, the timing may be immediately before the selection unit 64 selects the radiographic image. Further, for example, the priority setting process may be performed in advance before the image processing for generating and projecting the projection image P for guidance is performed, which will be described below. Furthermore, the setting of the priority for each selection criterion does not need to be performed whenever the radiographic image of the breast is captured, and the priority information 53B stored in the storage unit 52 may be used repeatedly.

Moreover, in the console 12 according to this embodiment, the CPU 50A of the control unit 50 executes the scoring processing program included in the image processing program 51 stored in the ROM 50B to function as the scoring unit 62.

The scoring unit 62 has a function of scoring each of a plurality of radiographic images captured in the past on the basis of, for example, the imaging information. Specifically, the scoring unit 62 scores each of a plurality of radiographic images captured in the past using a point addition method which adds a higher score as the degree of suitability of the radiographic image for generating the projection image P for guidance in the current imaging becomes higher. The scores corresponding to each of the plurality of radiographic images captured in the past which are given by the scoring unit 62 are stored as the scoring information 53C in the storage unit 52.

Figure 8:
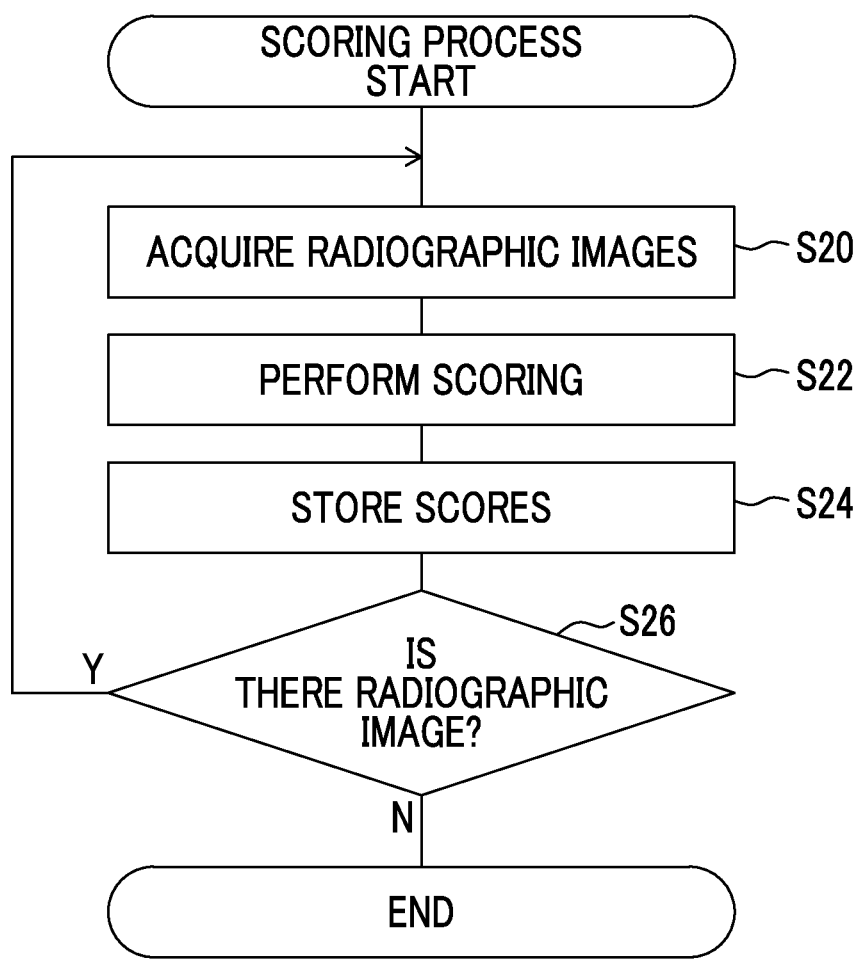
FIG. 8 is a flowchart illustrating an example of the flow of a scoring setting process.

Here, the operation of the console 12 related to scoring will be described. In the console 12 according to this embodiment, for example, the CPU 50A of the control unit 50 executes the scoring processing program included in the image processing program 51 stored in the ROM 50B to perform the scoring process whose example illustrated in FIG. 8. FIG. 8 is a flowchart illustrating an example of the flow of the scoring process performed in the console 12 according to this embodiment.

In Step S20 of FIG. 8, the scoring unit 62 acquires the radiographic images captured in the past. For example, the scoring unit 62 acquires the radiographic images of the breast captured in the past with reference to the storage unit 52 and the PACS 3. In addition, in some cases, the number of corresponding radiographic images is enormous only in the definition of the radiographic images of the breast captured in the past. In this case, for example, limited conditions, such as the radiographic images of the same subject and the radiographic images captured within a predetermined time from the present, may be set, and the scoring unit 62 may acquire the radiographic images satisfying the limited conditions.

Then, in Step S22, the scoring unit 62 scores the radiographic images acquired in Step S20. As described above, the scoring unit 62 scores the radiographic images using the point addition method which adds a higher score as the degree of suitability of the radiographic image for generating the projection image P for guidance in the current imaging becomes higher. For example, the scoring unit 62 adds scores whenever each of the following conditions is satisfied: whether the subject is the same; whether the left and right breasts are the same; whether the angle of the arm portion 32 is the same; whether the CC imaging or the MLO imaging is the same; whether the type of the compression plate 40 used is the same; and whether the radiographer is the same. Further, for example, for the condition of the elapsed time from the capture of the radiographic image to the present time, the scoring unit 62 adds a higher score as the elapsed time becomes shorter. In addition, a method for scoring the radiographic images is not limited to the above, and the conditions used for scoring are not limited to the above conditions. For example, the scoring described in JP2010-51456A may be applied to this embodiment. JP2010-51456A discloses a technique which scores a radiographic image according to whether or not positioning is properly performed.

Then, in Step S24, the scoring unit 62 stores the scores obtained by the scoring in Step S22 as the scoring information 53C in the storage unit 52. For example, the scoring unit 62 stores the score associated with identification information for identifying the radiographic image as the scoring information 53C. In addition, instead of storing the scoring information 53C, information indicating the score may be given to the stored image data of the radiographic image.

Then, in Step S26, the scoring unit 62 determines whether or not there is a selectable radiographic image. In a case in which a selectable radiographic image remains, the determination result in Step S26 is "Yes", and the process returns to Step S20. Then, the processes in Steps S20 to S24 are repeated. On the other hand, in a case in which no selectable radiographic images remain, the determination result in Step S26 is "No", and the scoring process illustrated in FIG. 8 ends.

Figure 9:
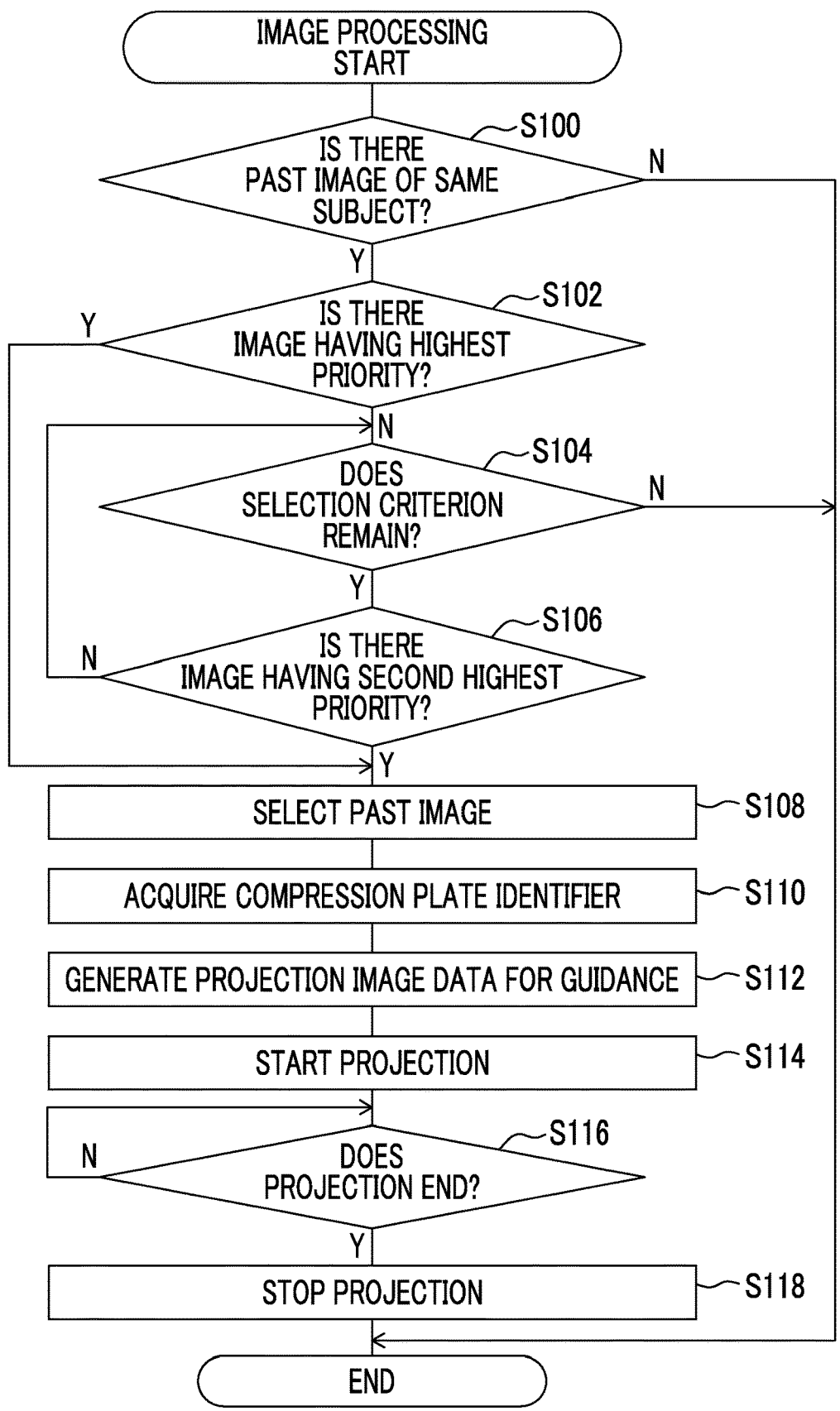
FIG. 9 is a flowchart illustrating an example of the flow of image processing according to a first embodiment.

Next, the operation of the console 12 in the projection of the projection image P for guidance by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selected imaging menu, it performs image processing illustrated in FIG. 9. In the console 12 according to this embodiment, for example, the CPU 50A of the control unit 50 executes the image processing program 51 stored in the ROM 50B to perform the image processing whose example is illustrated in FIG. 9. FIG. 9 is a flowchart illustrating an example of the flow of the image processing performed in the console 12 according to this embodiment.

In Step S100 of FIG. 9, the selection unit 64 determines whether or not there is a radiographic image captured in the past for the same subject as the subject corresponding to the breast to be imaged. The determination result in Step S100 is "No" in a case in which the selection unit 64 determines that there is no radiographic image of the same subject captured in the past with reference to the storage unit 52 and the PACS 3 as described above. In this case, the image processing illustrated in FIG. 9 ends.

On the other hand, in a case in which there is a radiographic image of the same subject captured in the past, the determination result in Step S100 is "Yes", and the process proceeds to Step S102.

In Step S102, the selection unit 64 further determines whether or not there is a radiographic image satisfying the selection criterion having the highest priority with reference to the priority information 53B stored in the storage unit 52 as described above. In a case in which there is a radiographic image satisfying the selection criterion having the highest priority, the determination result in Step S102 is "Yes", and the process proceeds to Step S108. On the other hand, in a case in which there is no radiographic image satisfying the selection criterion having the highest priority, the determination result in Step S102 is "No", and the process proceeds to Step S104.

In Step S104, the selection unit 64 determines whether or not the selection criterion which has not yet been used for the determination in Step S102 remains. Specifically, the selection unit 64 determines whether or not the selection criterion to which the priority has been set and which has not yet been used for the determination in Step S102 remains with reference to the priority information 53B. In a case in which the selection criterion that has not yet been used for the determination does not remain, that is, in a case in which the determination in Step S102 is performed for all of the selection criteria, the determination result in Step S104 is "No". In this case, since there is no radiographic image satisfying the selection criteria, the image processing ends. Further, in this case, the user may be presented with, for example, information indicating that the projection image P for guidance is not projected.

On the other hand, in a case in which the selection criterion that has not yet been used for the determination remains, the determination result in Step S104 is "Yes", and the process proceeds to Step S106. In Step S106, the selection unit 64 further determines whether or not there is a radiographic image satisfying the selection criterion having the second highest priority with reference to the priority information 53B stored in the storage unit 52. In a case in which there is no radiographic image satisfying the selection criterion having the second highest priority, the determination result in Step S106 is "No", and the process returns to Step S104. On the other hand, in a case in which there is a radiographic image satisfying the selection criterion having the second highest priority, the determination result in Step S106 is "Yes", and the process proceeds to Step S108.

In Step S108, the selection unit 64 selects a radiographic image that was captured in the past and satisfies the above-mentioned selection criterion. The selection unit 64 acquires the image data of the selected radiographic image. As described above, in this embodiment, according to the selection criterion having the highest priority, the selection unit 64 acquires the image data of the radiographic image of the opposite breast captured most recently (within 1 hour). In addition, according to the selection criterion having the second highest priority, the selection unit 64 acquires image data indicating the radiographic image of the breast on the same side. Further, according to the selection criterion having the third highest priority, the selection unit 64 acquires image data indicating the radiographic image captured by the CC imaging or the MLO imaging which is the same as the current imaging. Furthermore, according to the selection criterion having the fourth highest priority, the selection unit 64 acquires image data indicating the radiographic image having the highest score given by the scoring unit 62. Moreover, according to the selection criterion having the fifth highest priority, the selection unit 64 acquires image data indicating the radiographic image captured most recently.

Then, in Step S110, the generation unit 66 acquires the compression plate identifier from the mammography apparatus 10 as described above.

Then, in Step S112, the generation unit 66 generates image data indicating the projection image P for guidance as described above. In some cases, the size of the compression portion 41 and the size of the projection surface 45 vary depending on the type of the compression plate 40. Therefore, in this embodiment, the projector 48 projects the projection image P for guidance corresponding to the type of the compression plate 40. For example, in this embodiment, information (not illustrated) indicating the size of the projection image P for guidance corresponding to the compression plate identifier is stored in the storage unit 52. As described above, the generation unit 66 generates image data indicating the projection image P for guidance that is generated by the skin line image generated from the radiographic image selected in Step S108 and has a size corresponding to the compression plate identifier acquired in Step S110. For example, the generation unit 66 may generate the projection image P for guidance using either the first generation method described with reference to FIG. 5A or the second generation method described with reference to FIG. 5B and perform trimming to a size corresponding to the compression plate identifier to generate the projection image P for guidance.

Figure 10:
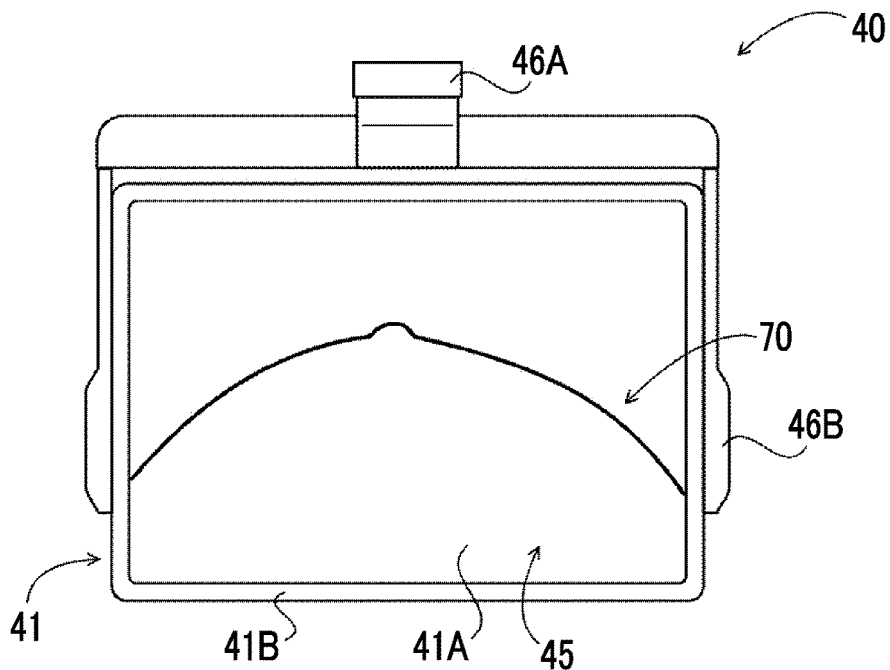
FIG. 10 is a diagram illustrating an example of a state displayed by a projection image projected onto a projection surface of the compression plate.

Then, in Step S114, the projection control unit 68 starts the projection of the projection image P for guidance. Specifically, the projection control unit 68 outputs the image data of the projection image P for guidance generated in Step S112 to the mammography apparatus 10 through the I/F unit 54. In the mammography apparatus 10, in a case in which the image data of the projection image P for guidance is input, the control unit 20 performs control to direct the projection unit 48B of the projector 48 to project the projection image P for guidance corresponding to the image data. An image indicating the skin line of the breast is displayed in the range of the irradiation field 102 on the projection surface 45 of the compression plate 40 attached to the compression unit 36 of the mammography apparatus 10 according to the projection image P for guidance by this control. FIG. 10 illustrates an example of a skin line 70 displayed on the projection surface 45 of the compression plate 40. The user compresses the breast of the subject positioned with reference to the position of the displayed skin line with the compression plate 40.

In addition, the timing when the projection image P for guidance is projected is not limited. For example, in a case in which the user inputs a projection start instruction, the projector 48 may start to project the projection image P for guidance. Further, for example, in a case in which the compression plate 40 starts to be moved in the compression direction, the projector 48 may start to project the projection image P for guidance.

Then, in Step S116, the projection control unit 68 determines whether or not to end the projection of the projection image P for guidance. For example, in this embodiment, the projection of the projection image P for guidance ends in a case in which end conditions are satisfied. The end conditions include, for example, a condition in which the projection of the projection image P for guidance ends in a case in which the user inputs an instruction to end the projection of the projection image P for guidance. In addition, the end conditions include, for example, the timing when the emission of the radiation R by the radiation source 37R starts or the timing when the emission ends. The determination result in Step S116 is "No" until the end conditions are satisfied. On the other hand, in a case in which the end conditions are satisfied, the determination result in Step S116 is "Yes", and the process proceeds to Step S118.

In Step S118, the projection control unit 68 ends the projection of the projection image P for guidance. Specifically, the projection control unit 68 outputs a projection end signal for ending the projection of the projection image P for guidance to the mammography apparatus 10 through the I/F unit 54. In the mammography apparatus 10, in a case in which the projection end signal is input, the control unit 20 ends the projection of the projection image P for guidance by the projection unit 48B of the projector 48. Specifically, the emission of the projection light for projecting the projection image P for guidance is stopped. In a case in which the projection of the projection image P for guidance is ended, the supply of power to the power supply unit 48A is cut off to turn off the power supply unit 48A. In a case in which the process in Step S118 ends, the image processing illustrated in FIG. 9 ends.

In addition, in this embodiment, in the image processing illustrated in FIG. 9, in a case in which there is no radiographic image of the same subject captured in the past, the projection image P for guidance is not projected. However, the present disclosure is not limited to this embodiment. In other words, the process in Step S100 of the image processing may be omitted. Further, in this case, as one of the selection criteria whose priorities can be selected, a selection criterion of selecting the radiographic image of the same subject captured in the past may be provided.

Second Embodiment

In this embodiment, an aspect in which a mode for capturing a radiographic image is different from that in the first embodiment will be described. In the first embodiment, the aspect in which a radiographic image used to generate the projection image P for guidance is selected from a plurality of radiographic images captured in the past using the selection criterion corresponding to the priority has been described. In contrast, in this embodiment, the following aspect will be described: in a case in which imaging is performed under specific imaging conditions, a radiographic image used to generate the projection image P for guidance is selected from a plurality of radiographic images captured in the past using a predetermined selection criterion.

In addition, in this embodiment, as an example of the specific imaging conditions, an imaging condition will be described in which the images of the left and right breasts are captured by a series of imaging operations (hereinafter, referred to as left-right sequential imaging).

Since the configurations of the mammography apparatus 10 and the console 12 according to this embodiment are the same as the configurations of the mammography apparatus 10 and the console 12 (see FIG. 3) according to the first embodiment, the description thereof will not be repeated.

Figure 11:
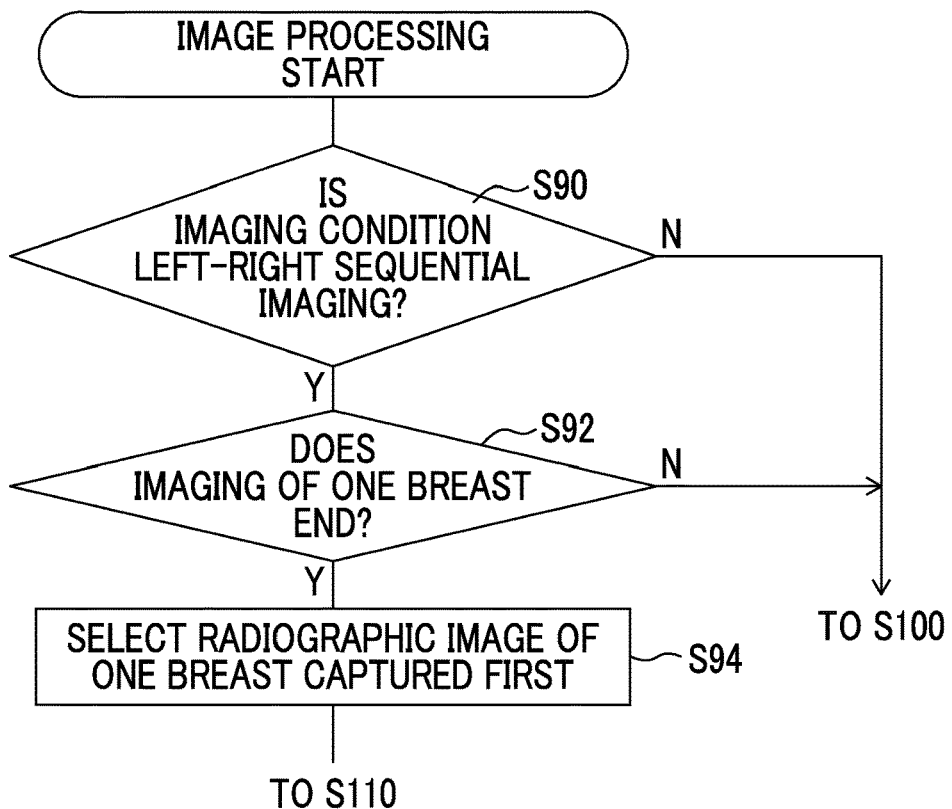
FIG. 11 is a flowchart illustrating an example of the flow of image processing according to a second embodiment.

On the other hand, since this embodiment differs from the first embodiment in image processing performed in the console 12, the image processing according to this embodiment will be described. FIG. 11 is a flowchart illustrating an example of the flow of the image processing performed in the console 12 according to this embodiment.

In Step S90, the selection unit 64 determines whether or not the indicated imaging condition is the left-right sequential imaging in which the images of the left and right breasts are captured by a series of imaging operation with reference to the imaging menu. In a case in which other imaging conditions are indicated in the imaging menu, the determination result in Step S90 is "No", and the process proceeds to Step S100 of the image processing (see FIG. 9) according to the first embodiment. On the other hand, in a case in which the imaging condition indicated in the imaging menu is the left-right sequential imaging, the determination result in Step S90 is "Yes", and the process proceeds to Step S92.

In Step S92, the selection unit 64 determines whether or not the capture of the radiographic image of either the left breast or the right breast ends in the left-right sequential imaging. In the left-right sequential imaging, in a case in which first imaging is performed, that is, in a case in which the first imaging of two imaging operations is performed, the determination result in Step S92 is "No", and the process proceeds to Step S100 of the image processing (FIG. 9) according to the first embodiment.

On the other hand, in a case in which the image of the right breast is captured previously and the image of the left breast is captured this time, or in a case in which the image of the left breast is captured previously and the image of the right breast is captured this time, the determination result in Step S92 is "Yes", and the process proceeds to Step S94.

In Step S94, the selection unit 64 selects the radiographic image of one breast captured previously. In a case in which the image of the right breast is captured previously and the image of the left breast is captured this time, the selection unit 64 selects the radiographic image of the right breast captured previously. Further, in a case in which the image of the left breast is captured previously and the image of the right breast is captured this time, the selection unit 64 selects the radiographic image of the left breast captured previously.

In accordance with the above, in this embodiment, in the left-right sequential imaging, in a case in which the radiographic image of one of the left breast and the right breast is captured and then the radiographic image of the other breast is captured, the projection image P for guidance based on the radiographic image of one breast captured first is projected onto the projection surface 45 of the compression plate 40 that compresses the other breast.

In many cases, the left and right breasts of the same subject are symmetric with respect to the center line of the subject in the CC direction and are similar in size and shape. Therefore, the projection image P for guidance which is reversed in the left-right direction is generated using the radiographic image of the breast captured most recently, which makes it possible to project an appropriate projection image P for guidance in the positioning of the opposite breast to be imaged.

In addition, in a case in which the radiographic image of either the left breast or the right breast is captured first, the projection image P for guidance based on the radiographic image of the breast selected by a predetermined selection criterion on the basis of the imaging information related to the capture of a plurality of radiographic images is projected onto the projection surface 45 of the compression plate 40 that compresses one breast. Therefore, it is possible to select an appropriate radiographic image used to generate the projection image P for guidance even in the first imaging performed in a state in which the radiographic image of the opposite breast on the left and right sides captured in most recently is absent.

As described above, the console 12 according to each of the above-described embodiments comprises the CPU 50A which corresponds to at least one processor. The CPU 50A selects a radiographic image used to guide the positioning of the breast to be imaged by the mammography apparatus 10, which irradiates the breast compressed by the compression plate 40 with the radiation R to capture a radiographic image, from a plurality of radiographic images of the breast on the basis of the imaging information related to the capture of the plurality of radiographic images. In addition, the CPU 50A generates the projection image P for guiding the positioning of the breast to be imaged from the selected radiographic image. Further, the CPU 50A controls the mammography apparatus 10 such that the projector 48 projects the generated projection image P for guidance.

As described above, the console 12 according to each of the above-described embodiments generates the projection image P for guiding the positioning of the breast to be imaged, using a radiographic image selected from a plurality of radiographic images of the breast on the basis of the imaging information related to the capture of the plurality of radiographic images. Therefore, according to the console 12 of this embodiment, the projection image for guidance generated by an appropriate radiographic image selected from a plurality of radiographic images captured in the past can be projected in the current imaging.

Further, in each of the above-described embodiments, the aspect in which the radiographic image is selected on the basis of the selection criterion corresponding to the priority has been described. However, the radiographic image may be selected according to a specific selection criterion, without using the priority. For example, the selection unit 64 may select a radiographic image on the basis of only the criterion of selecting the radiographic image of the opposite breast captured most recently (within 1 hour) which has been described above as the selection criterion having the highest priority. In addition, for example, the selection unit 64 may select a radiographic image on the basis of only the criterion of selecting the radiographic image of the breast on the same side which has been described above as the selection criterion having the second highest priority. Further, for example, the selection unit 64 may select a radiographic image on the basis of only the criterion of selecting the radiographic image captured in the CC imaging or the MLO imaging that is the same as the current imaging which has been described above as the selection criterion having the third priority. Furthermore, for example, the selection unit 64 may select a radiographic image on the basis of only the criterion for selecting the radiographic image with the highest score given by the scoring unit 62 which has been described above as the selection criterion having the fourth highest priority. Moreover, for example, the selection unit 64 may select a radiographic image on the basis of only the criterion of selecting the radiographic image captured most recently which has been described above as the selection criterion having the fifth highest priority. In addition, for example, in the case of the second embodiment, the image processing may end in a case in which the determination result in Step S90 is "No" or in a case in which the determination result in Step S92 is "No" in the image processing (see FIG. 11).

Further, in each of the above-described embodiments, the aspect has been described in which the skin line image which is an example of the image guiding at least one of the shape of the breast in the compressed state or the position of the breast in the compressed state is applied as an example of the projection image P for guidance. However, the present disclosure is not limited to this aspect. The projection image P for guidance is not limited as long as it is an image which is projected such that information for guiding the positioning of the breast to be compressed by the user with the compression plate 40 can be displayed. For example, in a case in which the projection image P for guidance is an image for guiding at least one of the shape of the breast in the compressed state or the position of the breast in the compressed state, it may be an image indicating the position of the nipple of the breast. Further, in the aspect in which the projection image P for guidance is the skin line image, the entire skin line of the breast is represented by a line (see FIG. 10). However, the present disclosure is not limited to this aspect. A portion of the skin line of several parts on the chest wall side and the nipple side may be illustrated.

Furthermore, for example, the projection image P for guidance may be a projection image for displaying information related to the subject, such as the name of the subject, information related to compression, such as compression pressure or the height of the compression plate 40, information related to the radiographer, information related to the imaging date, and the like on the projection surface 45 of the compression plate 40, or may be an image indicating characters or numbers. In addition, the projection image P for guidance may be a projection image for displaying a plurality of information items. Further, the projection image P for guidance may be a radiographic image of the breast.

Further, in each of the above-described embodiments, the aspect in which the size of the projection image P for guidance is equal to or less than the size of the projection surface 45 has been described. However, the size of the projection image P for guidance may be equal to or greater than the size of the projection surface 45 of the compression plate 40. That is, the projection image P for guidance may be projected onto the imaging surface 30A of the imaging table 30. Furthermore, the projection image P for guidance may be projected only on the imaging table 30. Further, for example, the projection image P for guidance may be displayed on the wall portion 41B of the compression plate 40.

Further, in each of the above-described embodiments, the aspect in which the image to be selected by the selection unit 64 of the console 12 is a radiographic image has been described. However, the image to be selected is not limited to the radiographic image and may be any image of the breast. For example, the image to be selected may be an image obtained by sonography. In addition, it is preferable that the image to be selected is an image captured in a compressed state similarly to the compression plate 40 of the mammography apparatus 10.

Further, the configuration for projecting the projection image P for guidance in the mammography apparatus 10 is not limited and is not limited to the aspect using the projector 48 described in each of the above-described embodiments. Further, in a case in which the projector 48 is applied, the configuration of the projector 48 is not limited. For example, in each of the above-described embodiments, the aspect in which the projection image P for guidance projected from the projector 48 is directly projected onto the projection surface 45 has been described. However, the projection image P may be reflected from a mirror or the like to be projected onto the projection surface 45. In this case, the direction in which the projection image P for guidance is projected can be adjusted by the mirror or the like. Furthermore, for example, a shutter or the like that blocks the projection light may be provided in front of the projection unit 48B of the projector 48. In this case, the shutter may be opened or closed to control the projection of the projection image P for guidance onto the projection surface 45. Specifically, in a case in which the projection of the projection image P for guidance is started, control is performed such that the shutter is opened to transmit the projection light. On the other hand, in a case in which the projection of the projection image P for guidance is ended, control is performed such that the shutter is closed to block the projection light.

Further, in each of the above-described embodiments, the aspect in which the console 12 is an example of the image processing device according to the present disclosure has been described. However, devices other than the console 12 may have the functions of the image processing device according to the present disclosure. In other words, for example, the mammography apparatus 10 or an external device other than the console 12 may have some or all of the functions of the receiving unit 60, the scoring unit 62, the selection unit 64, the generation unit 66, and the projection control unit 68.

Further, in each of the above-described embodiments, for example, the following various processors can be used as the hardware structure of processing units performing various processes such as the receiving unit 60, the scoring unit 62, the selection unit 64, the generation unit 66, and the projection control unit 68. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the image processing program 51 is stored (installed) in the ROM 50B in advance has been described. However, the present disclosure is not limited thereto. The image processing program 51 may be recorded on a recording medium, such as a compact disc read only memory (CD-ROM), a digital versatile disc read only memory (DVD-ROM), or a universal serial bus (USB) memory, and then provided. In addition, the image processing program 51 may be downloaded from an external device through a network.

What is claimed is:

1. An image processing device comprising:
   at least one processor that is configured to:
   select an image used to guide positioning of a breast to be imaged by a mammography apparatus, which irradiates the breast compressed by a compression member with radiation to capture a radiographic image, from a plurality of images of the breast on the basis of imaging information related to a capture of the plurality of images;
   generate a projection image for guiding the positioning of the breast to be imaged from the selected image;
   control the mammography apparatus such that an image projection unit projects the generated projection image for guidance;
   receive a setting of a priority of a selection criterion of selecting the image used for guidance on the basis of the imaging information, and select the image used for guidance which satisfies the selection criterion from the plurality of images on the basis of the priority;

acquire a compression plate identifier for identifying a type of the compression member attached to the mammography apparatus; and generate the projection image for guidance in accordance with the type of the compression member identified by the compression plate identifier.

2. The image processing device according to claim 1, wherein the imaging information includes information indicating a subject with the breast to be imaged, and the processor is configured to select an image of the breast of the same subject as the subject with the breast to be imaged from the plurality of images.

3. The image processing device according to claim 1, wherein the imaging information includes information indicating an imaging date and time, and the processor is configured to select an image with a latest imaging date and time from the plurality of images.

4. The image processing device according to claim 3, wherein the imaging information further includes information indicating whether the breast to be imaged is a left breast or a right breast of the subject, and in a case in which left and right sides of the breast of the selected image and the breast to be imaged are opposite to each other, the processor is configured to generate the projection image for guidance in which the left and right sides of the selected image are reversed.

5. The image processing device according to claim 4, wherein, after reversing the left and right sides of the selected image, the processor is configured to extract a feature image indicating a shape feature of the breast from the reversed image to obtain the projection image for guidance.

6. The image processing device according to claim 4, wherein the processor is configured to extract a feature image indicating a shape feature of the breast from the selected image and reverses the extracted feature image to generate the projection image for guidance.

7. The image processing device according to claim 1, wherein the imaging information includes information indicating whether or not each of left and right breasts of the subject is imaged by a series of imaging operations of the mammography apparatus, and in a case in which the series of imaging operations is performed and the plurality of images include a radiographic image captured first by the series of imaging operations, the processor is configured to select the radiographic image captured first and reverses left and right sides of the selected image to generate the projection image for guidance.

8. The image processing device according to claim 1, wherein the processor is configured to select an image having the same imaging information as that in imaging to be performed from the plurality of images.

9. The image processing device according to claim 1, wherein the processor is configured to score each of the plurality of images on the basis of the imaging information and selects an image with a highest score from the plurality of images.

10. The image processing device according to claim 1, wherein the imaging information is information indicating at least one of an imaging date and time, a subject corresponding to the breast, a compression pressure applied to the breast, whether the breast is a left breast or a right breast, or an imaging direction.

11. The image processing device according to claim 1, wherein the projection image for guidance is an image for guiding at least one of a shape of the breast in the compressed state or a position of the breast in the compressed state.

12. A non-transitory computer-readable storage medium storing an image processing program that causes a computer to perform a process comprising:

selecting an image used to guide positioning of a breast to be imaged by a mammography apparatus, which irradiates the breast compressed by a compression member with radiation to capture a radiographic image, from a plurality of images of the breast on the basis of imaging information related to a capture of the plurality of images;

generating a projection image for guiding the positioning of the breast to be imaged from the selected image;

controlling the mammography apparatus such that an image projection unit projects the generated projection image for guidance;

receiving a setting of a priority of a selection criterion of selecting the image used for guidance on the basis of the imaging information, and selecting the image used for guidance which satisfies the selection criterion from the plurality of images on the basis of the priority;

acquiring a compression plate identifier for identifying a type of the compression member attached to the mammography apparatus; and generating the projection image for guidance in accordance with the type of the compression member identified by the compression plate identifier.

* * * * *